United States Patent [19]

Miller et al.

[11] 4,259,339

[45] Mar. 31, 1981

[54] CYANOARALKYLHETEROCYCLIC COMPOUNDS

[75] Inventors: George A. Miller, Maple Glen; Hak-Foon Chan, Doylestown, both of Pa.

[73] Assignee: Rohm and Haas Company, Philadelphia, Pa.

[21] Appl. No.: 16,053

[22] Filed: Feb. 28, 1979

Related U.S. Application Data

[62] Division of Ser. No. 840,072, Oct. 6, 1977, Pat. No. 4,167,576.

[51] Int. Cl.$^3$ ............... A01N 43/64; C07D 249/08
[52] U.S. Cl. .................................. 424/269; 548/262
[58] Field of Search ............ 260/308 R; 424/269; 548/262

[56] References Cited

U.S. PATENT DOCUMENTS

| | | | |
|---|---|---|---|
| 3,826,836 | 7/1974 | Buchel et al. | 548/341 |
| 4,073,921 | 2/1978 | Miller et al. | 548/341 |

OTHER PUBLICATIONS

Meiser et al., Chem. Abstracts, vol. 77, Abstract No. 114410d (1972).
Sawa et al., Chem. Abstracts, vol. 78, Abstract No. 16239f (1973).
Fieser et al., Organic Chemistry, (D. C. Heath & Co., Boston, 1950), Second Edition, pp. 148–152, 292–293.

*Primary Examiner*—Alton D. Rollins
*Attorney, Agent, or Firm*—Bernard J. Burns

[57] ABSTRACT

This invention relates to phenoxy, phenylthio, phenylsulfinyl and phenylsulfonyl substituted cyano aralkyl imidazoles and triazoles, their enantiomorphs, acid addition salts and metal salt complexes thereof as well as their methods of preparation and use as broad spectrum systemic fungicides useful in controlling phytopathogenic fungi.

6 Claims, No Drawings

CYANOARALKYLHETEROCYCLIC COMPOUNDS

This is a division of application Ser. No. 840,072 filed Oct. 6, 1977, now U.S. Pat. No. 4,167,576 issued Sept. 11, 1979.

SUMMARY OF THE INVENTION

This invention relates to phenoxy, phenylthio, phenylsulfinyl and phenylsulfonyl substituted cyanoaralkylheterocyclic compounds of the formula

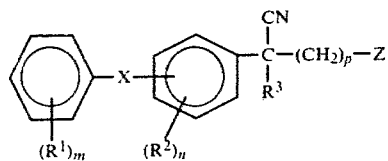

wherein $R^1$ and $R^2$ are independently hydrogen, halogen, alkyl, alkoxy, nitro, cyano, trihalomethyl, monoalkylamino and dialkylamino; $R^3$ is hydrogen, alkyl, cycloalkyl, alkenyl, alkynyl, cycloalkenyl, optionally substituted aryl and optionally substituted aralkyl; Z is a heterocyclic moiety; X is $CH_2$, O, S, SO and $SO_2$; m and n are independently zero or the integer 1 or 2; and p is an integer from 1 to 5; and the agroromically acceptable acid addition salts and metal salt complexes thereof.

DETAILED DESCRIPTION OF THE INVENTION

This invention relates to novel substituted cyanoaralkylheterocyclic compounds, and the enantiomorphs, acid addition salts and metal salt complexes of Formula (I) wherein $R^1$ and $R^2$ are independently selected from the group consisting of hydrogen, halogen, ($C_1$ to $C_4$) alkyl, ($C_1$ to $C_4$) alkoxy, nitro, cyano, trihalomethyl, mono ($C_1$ to $C_4$) alkylamino and di ($C_1$ to $C_4$) alkylamino; $R^3$ is selected from the group consisting of hydrogen, ($C_1$ to $C_{12}$) alkyl, ($C_3$ to $C_8$) cycloalkyl, ($C_2$ to $C_8$) alkenyl, ($C_2$ to $C_8$) alkynyl, ($C_5$ to $C_7$) cycloalkenyl, optionally substituted ($C_6$ to $C_{10}$) aryl and optionally substituted ($C_7$ to $C_{11}$) aralkyl; Z is a heterocyclic moiety selected from the group consisting of 1-imidazoyl, 1-(1,2,4-triazole) and 4-(1,2,4-triazole); X is selected from the group consisting of $CH_2$, O, S, SO and $SO_2$; m and n are independently zero or the integer 1 or 2; and p is an integer from 1 to 5.

The terms "alkyl", "alkenyl", "alkynyl", "alkoxy" and "mono and dialkylamino" as used in the present specification and claims is meant to define both branched and straight chained hydrocarbon moieties. Typical substituents encompassed by these terms include methyl, ethyl, propyl, isopropyl, n-butyl, sec-butyl, isobutyl, vinyl, allyl, methallyl, propargyl, methoxy, ethoxy, isopropoxy, methylamino, ethylamino, propylamino, sec-butylamino, diemethylamino, diethylamino, di-n-propylamino, di-n-butylamino, di-sec-butylamino and the like.

The term "aryl" as used in the present specification and claims is meant to define both phenyl and naphthyl groups preferably phenyl. Likewise, the term "substituted aryl" is meant to define phenyl and naphthyl groups, preferably phenyl groups substituted with up to three substituents, preferably with up to two substituents, selected from the group consisting of halogen, preferably chlorine, ($C_1$ to $C_4$) alkyl, preferably methyl, ($C_1$ to $C_4$) alkoxy, preferably methoxy, and nitro. Typical substituents encompassed by the terms "aryl" and "substituted aryl" include phenyl, naphthyl, chlorophenyl, bromophenyl, chloronaphthyl, bromonaphthyl, tolyl, methylnaphthyl, anisyl, methoxynaphthyl, nitrophenyl, nitronaphthyl, 2-chloro-4-methylphenyl, 2-bromo-4-t-butylphenyl, 3,5-di-t-butylphenyl, 2,3-dinitrophenyl, 3,4-dimethoxyphenyl, 2,6-difluorophenyl, 2,5-diiodophenyl, 2,4,6-trimethylphenyl, 2,3,5-trimethoxyphenyl, 2-methyl-4-methoxy-6-chlorophenyl and the like.

The term "aralkyl" as used in the present specification and claims is meant to define benzyl, phenethyl, phenylpropyl, phenylisopropyl, phenyl-n-butyl, phenyl-sec-butyl, phenylneopentyl and naphthylmethyl, preferably benzyl. Likewise the term "substituted aralkyl" is meant to define benzyl, phenethyl, phenylpropyl, phenylisopropyl, phenyl-sec-butyl, phenylneopentyl and naphthylmethyl, preferably benzyl, substituted with up to three substituents, preferably with up to two substituents; selected from the group consisting of halogen, preferably chlorine, ($C_1$ to $C_4$) alkyl, preferably methyl, ($C_1$ to $C_4$) alkoxy, preferably methoxy, and nitro. Typical substituents encompassed by the terms "aralkyl" and "substituted aralkyl" include benzyl, naphthylmethyl, chlorobenzyl, bromobenzyl, fluorobenzyl, iodobenzyl, nitrobenzyl, methoxybenzyl, methylbenzyl, 2,4-dimethoxybenzyl, 3,5-dinitrobenzyl, 3,4-dimethylbenzyl, 2,5-dichlorobenzyl, 2,4-dibromobenzyl, 2,4,6-trichlorobenzyl, 2,4,6-trimethylbenzyl, and the like.

Another embodiment of this invention is the metal salt complexes of the formula

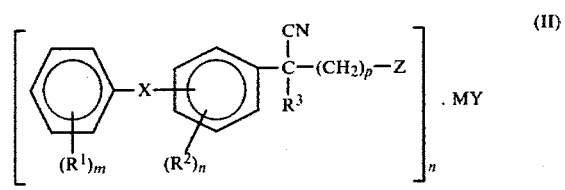

wherein $R^1$, $R^2$, $R^3$, X, Z, m, n and p are as defined in Formula (I) above, and M is a metal cation selected from Groups IIa, IVA, VA, IB, IIB, VIB, VIIB and VIII of the Periodic Table, Y is an anion counterion chosen in such a manner that the sum of the charges of the cation and anion equals zero; and a is an integer from 1 to 4.

A preferred embodiment of this invention are the compounds according to formula (I) wherein m and n equal zero and p is the integer one. A more preferred embodiment of this invention are the compounds according to formula (I) wherein m and n equal zero, p is the integer one and $R^3$ is ($C_1$ to $C_{12}$) alkyl. The most preferred compounds of this invention are the compounds according to formula (I) wherein m and n equal zero, p is the integer one, $R^3$ is ($C_1$ to $C_{12}$) alkyl and Z is the heterocyclic 1-imidazole.

The compounds, acid addition salts and metal salt complexes of this invention can be prepared by utilizing general synthetic routes described in the literature. In addition thereto, these compounds can be prepared by the following reaction sequence. The phenylacetonitrile starting materials are either commerically available or can be synthesized by methods well known in the art.

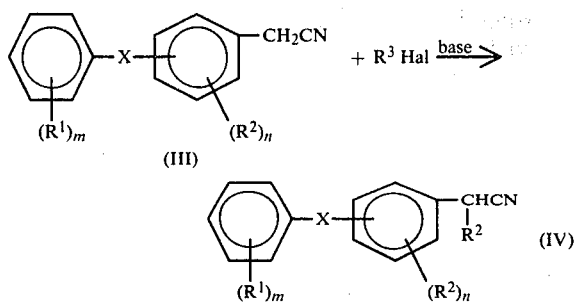

The appropriately substituted phenylacetonitrile (III), wherein $R^1$, $R^2$, X, m and n are as defined above, is reacted with a molar or excess amount of a suitable halide of the formula $R^3$ Hal wherein $R^3$ is as defined above and Hal can be chloride, bromide or iodide in a dipolar aprotic solvent such as dimethylsulfoxide, dimethylformamide and the like at temperatures from about 10° to 100° C. in the presence of a base such as sodium hydroxide, potassium hydroxide, triethylamine and the like to give the acetonitrile of formula (IV) which is then used in the next reaction.

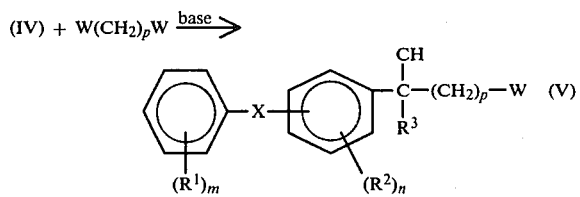

The appropriately substituted acetonitrile of formula (IV) is then added to a molar or excess amount of a compound of the structure $W(CH_2)_pW$, wherein W is chloro, bromo, iodo or sulfonate, in a dipolar aprotic solvent such as dimethylsulfoxide, dimethylformamide and the like at temperatures from about 10° C. to about 150° C. in the presence of a base, such as sodium hydroxide, potassium hydroxide, triethylamine and the like, to give the cyanoalkyl compound of formula (V) which is subsequently utilized in the following reaction.

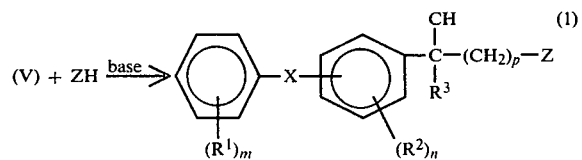

The cyanoalkyl compound (V) is reacted with a molar or excess amount of an imidazole or, 1-H-(1,2,4-triazole) either neat or in a dipolar aprotic solvent, either in the presence of a molar excess or a greater amount of the corresponding imidazole or triazole, or in the presence of a strong inorganic base, such as sodium hydroxide or potassium hydroxide, at temperatures from about 30° C. to about 200° C. to give the desired product of formula (I). In the case where a dipolar aprotic solvent and a metal hydroxide are utilized, an azeotroping solvent such as toluene or xylene can be utilized to azeotrope off the water of reaction and drive the reaction to completion.

When a metal salt such as the sodium salt of 1,2,4-triazole is used only the 1-substituted product is obtained.

When the starting material of Formula (V) is reacted with the 1H-1,2,4-triazole free base instead of its metal salt, at temperatures from about 50° C. to about 180° C. a mixture of 1-substituted and 4-substituted 1,2,4-triazoles is obtained and these triazoles can be easily separated by conventional chemical separation techniques such as extraction, chromatography, crystallization and the like.

In the case wherein X equals a sulfinyl or sulfonyl group, the phenylacetonitrile (III) wherein X equals a sulfur atom, can either be oxidized up to a sulfinyl or sulfonyl group utilizing one or two equivalents of a per-acid such as m-chloroperbenzoic acid, peracetic acid and the like, in an appropriate solvent such as methylene chloride, chloroform and the like, at temperatures from about $-15°$ C. to about room temperature; or it, (formula III, X=S) can be taken through the above reaction sequence (III→I) and then oxidized up to the appropriate product, (formula I, X=SO or $SO_2$).

Typical compounds encompassed by this invention include:
1-[2-Cyano-2-(3-phenylthiophenyl)hexyl]imidazole
1-[2-Cyano-2-cyclohex-2-enyl-2-(4-phenoxyphenyl) ethyl]imidazole
1-[2-Cyano-2-(4-phenylsulfinyl phenyl)-2-propargyl ethyl]imidazole
1-{2-Cyano-2-[3-(2'-chlorophenyl sulfonylphenyl]ethyl}imidazole
1-[2-Cyano-2-(2-cyano-4-phenoxyphenyl)propyl-]imidazolium chloride
1-{2-Cyano-2-cyclopentyl-2-[2-(3',5'-dichlorophenylthio phenyl)]ethyl}imidazole
1-[5-Cyano-5-(4-phenylsulfonylphenyl)nonyl]imidazole
1-{2-Cyano-4-phenyl-2-[2-(3'-chlorophenylsulfonyl)-4-methylphenyl]butyl}-1,2,4-triazole
1-[3-Cyano-4-(4-chlorophenyl)-3-(3-phenoxyphenyl)-butyl]-1,2,4-triazole
1-{2-Cyano-2-[3-trichloromethylphenyl]-2-[2-(4'-methylphenoxy)-3-nitrophenyl]ethyl}imidazole
1-[2-Cyano-2-allyl-2-(4-phenylthio-2-dibutylaminophenyl)ethyl]imidazolium chloride
1-{4-Cyano-7-phenyl-4-[3-(4'-fluorophenoxyphenyl]-heptyl}imidazole
1-[2-Cyano-3-(2-naphthyl)2-(4-phenylsulfonylphenyl)-propyl]-1,2,4-triazolium nitrate
1-[3-Cyano-3-(4-chloro-2-methylphenyl)-3-(3-benzylphenyl) propyl]-1,2,4-triazole
1-{3-Cyano-3-(4-bromophenyl)3-[2-ethyl-4-(2'-methoxyphenylthio) phenyl]propyl}-1,2,4-triazolium chloride
1-{2-Cyano-2-[3-(2,5-dimethylphenoxy) phenyl] tetradecanyl} imidazole
1-{3-Cyano-4-[2,4,6-trichlorophenyl]-3-[4-(4'-t-butylphenylsulfinyl) phenyl]butyl}imidazolium nitrate and the agronomically-acceptable enantiomorphs, acid addition salts and metal salt complexes thereof.

The addition salts of the cyanoaralkylheterocyclic compounds of this invention can be prepared by standard techniques well-known in the art. For example, the cyanoaralkylheterocyclic compound of formula (I) can be dissolved in an appropriate solvent such as diethyl ether, tetrahydrofuran, ethanol, methanol, and the like and treated at about room temperature with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above cyanoaralkyl-heterocyclic compounds can be prepared by adding dropwise, with stirring, a stoichiometric amount of a metal salt dissolved in an appropriate solvent as above, at about room temperature to a solution of the cyanoaralkylheterocyclic compound of formula (I) dissolved in a similarly appropriate solvent. The reaction mixture is briefly stirred and the solvent is removed under reduced pressure to give the metal salt complex of the respective cyanoaralkylheterocyclic compound of formula (II).

The metal salt complexes can also be prepared by mixing stoichiometric or excess amounts of the metal salt and the cyanoaralkylheterocyclic compound of formula (I) in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol or ethylene glycol and any aprotic dipolar solvent e.g., dimethylsulfoxide, acetonitrile, dimethylformamide, nitromethane or acetone.

The metal salt cations that may be used in these procedures typically include calcium, magnesium, manganese, copper, nickel, zinc, iron, cobalt, tin, cadmium, mercury, chromium, lead, barium, and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the solubilizing counterion in the metal salt.

Any metal containing fungicides can also be used to form metal salt complexes when used in place of metal salts. Typical metal containing fungicides that can be utilized in these procedures are: a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); b) copper-based fungicides such as cuprous oxide, copper naphthenate, and Bordeaux mixture, and c) miscellaneous fungicides such as: phenylmercuric acetate, N-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanamide.

The compounds of this invention possess an asymmetric carbon atom and are made as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples 1, 3, 5 and 8 are typical preparations of the compounds of the present invention and are provided merely to illustrate some of the methods of preparation of these compounds. These examples are not meant to be considered, in any way, as limitations of the breadth and scope of the present invention. The temperatures expressed in these examples are in degrees Centigrade.

EXAMPLE 1

Preparation of 1-[2-Cyano-2-(2-phenoxyphenyl)hexyl]imidazolium nitrate

A. 2-Phenoxybenzyl chloride

Into a three-necked 500 ml round-bottom flask are charged 25 g (0.125 mole) of o-phenoxy benzyl alcohol and 200 ml of benzene. To this solution is added 18 g (0.15 mole) of thionyl chloride dropwise with stirring. The reaction mixture is then heated to reflux for four hours. Solvent and excess thionyl chloride are removed under vacuum to give 30 g of product.

B. 2-(2-Phenoxyphenyl)hexanenitrile

Into a three-necked 300 ml round-bottom flask are charged 7.4 g (0.15 mole) of sodium cyanide and 80 ml of dimethyl sulfoxide. To this slurry is added 30 g (0.13 mole) of 2-phenoxybenzyl chloride dropwise. Reaction temperature increases from 24° to 44° C. The reaction mixture is stirred for an additional 1½ hours. To this reaction mixture is added 13.7 g (0.13 mole) of butyl chloride followed by dropwise addition of 34 g (0.4 mole) of 50% sodium hydroxide solution. After stirring for an additional ½ hour, reaction mixture is poured into 150 ml of water and extracted with hexane. The combined hexane extracts are washed with water and dried over $MgSO_4$. Solvent is evaporated to give 32 g of crude product. Material can be further purified by vacuum distillation (bp 149–60/0.25 mm).

C. 2-Cyano-2-(2-phenoxyphenyl)hexyl bromide

Into a three-necked 300 ml round bottom flask are charged 10 g (0.038 mole) of 2-(2-phenoxyphenyl)hexanenitrile, 6.6 g (0.038 mole) of dibromomethane and 50 ml of dimethyl sulfoxide. To this mixture with stirring is added 3.2 g (0.04 mole) of 50% sodium hydroxide solution dropwise. Reaction mixture is heated to give 60° for two hours and then poured into water and extracted with hexane. Combined hexane extracts are washed with water and dried over $MgSO_4$. Solvent is evaporated under vacuum to give 11.2 g of product.

D. 1-[2-Cyano-2-(2-phenoxyphenyl)hexyl]-imidazolium nitrate

Into a 100 ml round-bottom flask are charged 5 g (0.014 mole) of 2-cyano-2-(2-phenoxyphenyl)hexyl bromide and 5 g (0.07 mole) of imidazole. The mixture is heated at 160° for four hours. It is then poured into water and extracted with ether. The combined ether extracts are washed with water and dried over $Na_2SO_4$. Drying agent is filtered and to the filtrate is added conc. $HNO_3$ until it is strongly acidic. The nitric acid salt is collected by filtration and dried in a vacuum oven to give 3.4 g of desired product, mp 161°–3°.

nmr (DMSO): δ0.7–1.8 (m, 9H), 5.2 (S, 2H), 6.9–8.0 (m, 12H), 9.2 (S, 1H)

EXAMPLE 3

Preparation of 1-[2-Cyano-2-(4-phenylthiophenyl)hexyl]imidazole

A. 4-Phenylthiobenzyl Cyanide

Into a 1 L. round-bottom flask are charged 100 g (0.5 mole) of p-bromobenzyl cyanide, 103.5 g (0.6 mole) of cuprous thiophenoate (CA: 53, 16145d), 300 ml of quinoline, and 300 ml of pyridine. The mixture is heated at 200° overnight. It is then allowed to cool to 130° and poured into an ice-hydrochloric acid solution containing 1 kg of ice and 300 ml of conc. hydrochloric acid. The gummy black solid which separates from the aqueous solution is collected by filtration and then stirred with 800 ml of ether until most of the solid goes into solution. The insoluble inorganic copper is filtered and the filtrate is washed with 20% hydrochloric acid, water, saturated sodium chloride solution in that order and dried over MgSO4. Solvent is evaporated to give 65 g of an oil. Vacuum distillation (153°–165°/0.05 mm) provides 42 g of pure product.

B. 2-(4-Phenylthiophenyl)hexanenitrile

To a mixture of 41 g (0.18 mole) of 4-phenylthiobenzyl cyanide, 18 g (0.19 mole) of butyl chloride and 2 g of tetraethylammonium bromide is added 16 g (0.2 mole) of 50% sodium hydroxide solution dropwise at room temperature with stirring. The reaction mixture is heated at 85° for ½ hour and then an additional 16 g (0.2 mole) of 50% sodium hydroxide solution are added. Heating is continued for another ½ hour. The reaction mixture is poured into water and extracted with ether. The combined ether extracts are washed with water, saturated sodium chloride solution and dried over MgSO4. Solvent is evaporated to give 47 g of a crude product. Vacuum distillation (173°–180°/0.05 mm) gives 33 g of pure product.

C. 2-Cyano-2-(4-phenylthiophenyl)hexyl bromide

To a mixture of 31 g (0.1 mole) of 2-(4-phenylthiophenyl) hexanenitrile, 22 g (0.13 mole) of dibromomethane and 100 ml of dimethyl sulfoxide is added 12 g (0.15 mole) of 50% sodium hydroxide solution dropwise with stirring. Reaction mixture is stirred at 60° for ½ hour and then poured into water and extracted with ether. The combined ether extracts are washed with water and dried over MgSO4. Solvent is evaporated to give 38 g of product.

D. 1-[2-Cyano-2-(4-phenylthiophenyl)hexyl]imidazole

A mixture of 10 g (0.027 mole) of 2-cyano-2-(4-phenylthiophenyl)hexyl bromide and 8 g (0.13 mole) of imidazole is heated with stirring at 160° for four hours. The reaction mixture is poured into water and extracted with ether. The combined ether extracts are washed with water and dried over Na2SO4. The drying agent is filtered and to the filtrate is bubbled dry hydrogen chloride gas until solution is strongly acidic. The hydrochloride salt is washed with ether and back neutralized with dilute ammonium hydroxide solution to give 8 g of pure product.

nmr (CDCl3): δ0.7–2.4 (m, 9H), 4.3 (q, 2H), 6.8–7.5 (m, 12H).

EXAMPLE 5

Preparation of 1-[2-Cyano-2-(4-phenylsulfinylphenyl)hexyl]imidazole

To a solution of 4 g (0.01 mole) of 1-[2-cyano-2-(4-phenylthiophenyl)hexyl]imidazole in 25 ml of methylene chloride is added 2.5 g (0.012 mole) of 85% m-chloroperoxybenzoic acid in small portions at 0°. The mixture is stirred at room temperature overnight. To the reaction mixture is added conc. nitric acid until it is strongly acidic. To this solution is added 150 ml of anhydrous ether. The gummy solid precipitates are washed with ether and back neutralized with dilute NH4OH solution. The free base (3.5 g) thus obtained is a yellow solid, mp 55°–61°.

nmr (CDCl3): δ0.6–2.3 (m, 9H), 4.4 (q, 2H), 6.7–7.8 (m, 12H).

EXAMPLE 8

Preparation of 1-[2-Cyano-2-(3-phenoxyphenyl)hexyl]-1,2,4-triazolium chloride

A. 2-(3-Phenoxyphenyl)hexanenitrile

Into a three-necked 500 ml round-bottom flask are charged 35 g (0.17 mole) of m-phenoxybenzyl cyanide, 16.3 g (0.17 mole) of butyl chloride 4 g of tetraethylammonium bromide. To this mixture is added 27 g (0.34 mole) of 50% sodium hydroxide solution dropwise with stirring. The reaction mixture is heated at 90° for three hours. It is then poured into water and extracted with hexane. The combined hexane extracts are washed with water and dried over MgSO4. Solvent is evaporated to give 39 g of crude product. Vacuum distillation (149°–155°/0.2 mm) provides 24.7 g of pure product.

B. 2-Cyano-2-(3-phenoxyphenyl)hexyl bromide

To a solution of 10 g (0.038 mole) of 2-(3-phenoxyphenyl)hexanenitrile, 6.6 g (0.038 mole) of dibromomethane in 50 ml of dimethyl sulfoxide is added 3.2 g (0.04 mole) of 50% sodium hydroxide solution dropwise. The reaction mixture is stirred at 60° for one hour, poured into water and extracted with ether. The combined ether extracts are washed with water and dried over MgSO4. Solvent is evaporated to give 12 g of product.

C. 1-[2-Cyano-2-(3-phenoxyphenyl)hexyl]-1,2,4-triazolium chloride

Into a three-necked 300 ml round-bottom flask are charged 1.4 g (0.02 mole) of 1H-1,2,4-triazole, 0.8 g (0.02 mole) of sodium hydroxide pellets, 25 ml dimethylsulfoxide, and 15 ml xylene. The mixture is heated to 140° with stirring and water produced is azeotroped with a water separator. The solution is then cooled to 115° and 2-cyano-2-(3-phenoxyphenyl) hexyl bromide dissolved in 10 ml of xylene is added dropwise. Reaction mixture is stirred at 125° for one hour, poured into water, and extracted with ether. The combined ether extracts are washed with water and dried over Na2SO4. Drying agent is filtered and to the filtrate is bubbled dry hydrogen chloride gas until solution is strongly acidic. White solids formed are filtered to give 4.4 g of product, mp 157°–160°.

nmr (DMSO): δ0.8–2.4 (m, 9H), 4.9 (S, 2H); 6.7–8.2 (m, 11H) 8.8 (S, 1H).

Tables I and II give the empirical formula, structure, melting point in degrees centigrade and elemental analysis of some of the more representative compounds encompassed by the present invention which were synthesized by the above procedures.

TABLE I $$\text{Ph}-X-\text{Ph}-\underset{R^3}{\underset{|}{\overset{CN}{\underset{|}{C}}}}-CH_2-Z \cdot MY$$

| Ex. No. | Formula | X | $R^3$ | Z | MY |
|---|---|---|---|---|---|
| 1 | $C_{22}H_{23}N_3O \cdot HNO_3$ | 2-O | $C_4H_9n$ | imidazole | $HNO_3$ |
| 2 | $C_{22}H_{23}H_3O$ | 3-O | $C_4H_9n$ | imidazole | — |
| 3 | $C_{22}H_{23}N_3S$ | 4-S | $C_4H_9n$ | imidazole | — |
| 4 | $C_{22}H_{23}N_3S \cdot HCl$ | 4-S | $C_4H_9n$ | imidazole | HCl |
| 5 | $C_{22}H_{23}N_3OS$ | 4-SO | $C_4H_9n$ | imidazole | — |
| 6 | $C_{22}H_{23}N_3O_2S \cdot HNO_3$ | 4-SO$_2$ | $C_4H_9n$ | imidazole | $HNO_3$ |
| 7 | $C_{21}HH_{24}N_4O \cdot HNO_3$ | 2-O | $C_4H_9n$ | 1&4-triazole | HNO |
| 8 | $C_{21}H_{22}H_4O$ | 3-O | $C_4H_9n$ | 1-triazole | HCl |

TABLE II

| Example No. | MP | Elemental Analysis | | | Calc'd (Found) | | |
|---|---|---|---|---|---|---|---|
| | | C | H | Cl | N | O | S |
| 1 | 161-3 | 64.69 (62.16) | 5.92 (5.82) | | 13.72 (14.29) | 15.67 (17.48) | |
| 2 | oil | 76.49 (76.19) | 6.71 (6.85) | | 12.17 (11.04) | 4.63 (5.83) | |
| 3 | oil | 73.09 (71.37) | 6.41 (6.31) | | 11.62 (10.56) | | 8.87 (8.88) |
| 4 | 86-8 | 66.40 (65.25) | 6.08 (6.05) | 8.91 (8.24) | 10.56 (9.92) | | 8.06 (8.13) |
| 5 | 55-61 | 70.00 (68.68) | 6.14 (6.05) | | 11.13 (10.41) | 4.24 (5.23) | 8.49 (9.15) |
| 6 | 82-5 | 57.88 (58.08) | 5.30 (5.29) | | 12.27 (11.18) | 17.52 (17.82) | 7.02 (7.38) |
| 7 | 146-8 (dec) | 61.60 (59.64) | 5.66 (6.65) | | 17.11 (17.50) | 15.63 (15.97) | |
| 8 | 157-160 | 65.87 (65.40) | 6.06 (6.11) | 9.26 (9.21) | 14.63 (13.96) | 4.18 (5.24) | |

The cyanoaralkylheterocyclics, enantiomorphs, acid addition salts and metal salt complexes of this invention are broad-spectrum fungicides which possess a high degree of activity against assorted phytopathogenic fungi. These compounds, salts and complexes are particularly effective at rates of application from about 50 to about 2000 ppm in controlling phytopathogen fungi such as barley net blotch (*Helminthosporium teres*) on barley plants, grey mold (*Botrytis fabae*) on faba beans, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out by applying the compounds at an application rate of 300 ppm and spraying the plants to run off in a carrier volume of about 150 gallons/acre.

The general procedure is to take potted plants in proper condition of growth for susceptibility to the fungal disease to be evaluated, to spray these plants a moving belt with the compound to be evaluated and allow them to dry. The proper plants are then inoculated with the fungal spores and then allowed to incubate until the disease has developed and the percent control is read or estimated.

The following test methods are employed in evaluating the fungicidal activity of the compounds, enantimorphs, salts and complexes of this invention.

EXAMPLE A

Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greehouse at 70°-75° F. Treatment comparisons are made 6 to 7 days after inoculation. Typical barley net blotch symptoms initially appear as irregular sunken water-soaked areas which become necrotic as the lesions enlarge. Certain of the cyanoaralkylheterocyclics of this invention demonstrate complete control over *Helminthosporium teres* at application rates of 300 ppm.

EXAMPLE B

Broad Bean Gray Mold Leaf Spot (*Botrytis fabae*)

Broad bean plants (var. Vicia faba) are trimmed to a height of approximately 4.5 inches, 24 hours prior to chemical application. This procedure provides plants of a uniform height and permits rapid and uniform inoculation of the treated plants. Broad bean plants are inoculated by spraying the foliage with a herbicide belt sprayer. Inoculated plants are incubated in a humid environment at 75°-80° F. for 66 hours. Treatment comparisons are made 66 to 68 hours after inoculation. Typical broad bean gray mold leaf spot symptoms appear as regular circular to lanceolate lesions on plant leaves and stems. Certain of the cyanoaralkylheterocyclics of this invention demonstrate greater than 90% control over *Botrytis fabae* at application rates of 300 ppm.

EXAMPLE C

Bean Powdery Mildew (*Erysiphe polygoni*)

Bean plants (var. Drawf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. Certain of the cyanoaralkylheterocyclics of this invention demonstrate complete control over *Erysiphe polygoni* at application rates greater than 300 ppm.

EXAMPLE D

Grape Downy Mildew (*Plasmopora viticola*)

Grape seedlings (var. Siebel 1000) 4 to 5 inches tall are used. *Plasmopora viticola* is cultured on grape leaves for 7 days at 65°-75° F. The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth. Certain of the cyanoaralkylheterocyclics of this invention possess greater than 90% control over *Plasmopora viticola* at application rates of 300 ppm.

EXAMPLE E

Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°-85° F.) for 24 hours prior to being placed in a greenhouse environment. Treatment comparisons are made 7 to 8 days after inoculation. Initial rice blast lesions appear as small brown necrotic spots on the foliage. The typical lesion is ecliptical, 1 to 2 cm. long with a large necrotic gray center and brown margins. Certain of the cyanoaralkylheterocyclics of this invention possess complete control over *Piricularia oryzae* at application rates of 300 ppm.

EXAMPLE F

Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°-62° F. for 40 to 45 hours, prior to being placed in the greenhouse at 70°-75° F. Treatment comparisons are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the cyanoaralkylheterocyclics of the present invention possess complete control over *Phytophthora infestans* at application rates of 300 ppm.

EXAMPLE G

Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings. Certain of the cyanoaralkylheterocyclics of the present invention possess complete control over *Puccinia graminis* f. sp. *tritici* race 15B-2 at application rates of 300 ppm.

The cyanoaralkylheterocyclics, acid addition salts and metal salt complexes of the present invention can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[2-cyano-2-(4-phenylthiophenyl)hexyl]imidazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the cyanoaralkylheterocyclics, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable power with a finely divided carrier. Dust concentrates containing from about 20% to about 80% of the active ingredient are commonly made and are subsequently diluted to from about 1% to about 10% use concentration.

The cyanoaralkylheterocyclics, enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Typical fungicides which can be combined with the fungicides of this invention includes:

(a) dithiocarbamate and derivatives such as:
ferric dimethyldithiocarbamate (ferbam), zinc dimethyldithiocarbamate (ziram), maganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts;

(b) nitrophenol derivatives such as:
dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as:
N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine, diethyl phthalimidophosphorothioate, 4-butyl-1,2,4-triazole, 5-amino-2-[bis(dimethylamino)-phosphinyl]-3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,4-b]quinoxaline (thioquinox), methyl 1-(butylcarbamoyl)-2-benzimidazole carbamate (benomyl), 2-(4'-thiazolyl) benzimidazole (thiabendazole), 4-(2-chlorophenyl-hydrazono)-3-methyl-5-isoxazolone, pyridine-2-thiol-1-oxide, 8-hydroxyquinoline sulfate and metal salts thereof;
2,3-dihydro-5-carboxanilido-6-methyl-1,4-oxathiin-4,4-dioxide,
2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxyl-glutarimide (cycloheximide), dehydroacetic acid, N-(1,1,2,2-tetrachloroethylthio)-3a,4,7,7a-tetrahydrophthalimide(captafol), 5-butyl-2-ethylamino-4-hydroxy-6-methyl-pyrimidine (ethirimol), acetate of 4-cyclododecyl-2,6-dimethylmorpholine(-dodemorph), and 6-methyl-2-oxo-1,3-dithiolo[4,5-b]-quinoxaline(quinomethionate).

(d) miscellaneous halogenated fungicides such as:
tetrachloro-p-benzoquinone(chloranil), 2,3-dichloro-1,4-naphthoquinone(dichlone), 1,4-dichloro-2,5-dimethoxybenzene(chloroneb), 3,5,6-trichloro-o-anisic acid(tricamba), 2,4,5,6-tetrachloroisophthalonitrile (TCPN), 2,6-dichloro-4-nitroaniline(dichloran), 2-chloro-1-nitropropane, polychloronitrobenzenes such as: pentachloronitrobenzene (PCNB) and tetrafluorodichloroacetone;

(e) fungicidal antibiotics such as:
griseofulvin, kasugamycin and streptomycin;

(f) copper-based fungicides such as:
cuprous oxide, basic cupric chloride, basic copper carbonate, copper naphthenate, and Bordeaux mixture; and (g) miscellaneous fungicides such as:
diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzenediazo sodium sulfonate, ethyl isothiocyanate, 1-thiocyano-2,4-dinitrobenzene, 1-phenylthiosemicarbazide, nickel-containing compounds, calcium cyanamide, lime sulfur, sulfur, and 1,2-bis(3-methoxy-carbonyl-2-thioureido)benzene(thiophanatemethyl).

The cyanoaralkylheterocyclics, enantiomorphs, addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the cyanoaralkylheterocyclics of this invention will suggest themselves to those skilled in the art of agriculture and horticulture.

We claim:

1. A compound of the formula

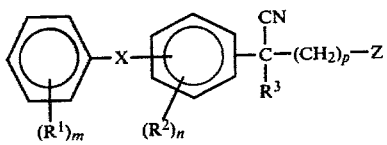

wherein
$R^1$ and $R^2$ are independently selected from the group consisting of hydrogen, halogen, ($C_1$ to $C_4$) alkyl, ($C_1$ to $C_4$) alkoxy, nitro, cyano, trihalomethyl, mono ($C_1$ to $C_4$) alkylamino and di ($C_1$ to $C_4$) alkylamino;

$R^3$ is selected from the group consisting of hydrogen, ($C_1$ to $C_{12}$) alkyl, ($C_3$ to $C_8$) cycloalkyl, ($C_2$ to $C_8$) alkenyl, ($C_2$ to $C_8$) alkynyl, ($C_5$ to $C_7$) cycloalkenyl, ($C_6$ to $C_{10}$) aryl and ($C_7$ to $C_{11}$) aralkyl or ($C_6$ to $C_{10}$) aryl and ($C_7$ to $C_{11}$) aralkyl substituted with up to three substituents selected from the group consisting of halogen, ($C_1$ to $C_4$) alkyl, ($C_1$ to $C_4$) alkoxy, and nitro;

Z is a heterocyclic moiety selected from the group consisting of 1-(1,2,4-triazole) and 4-(1,2,4-triazole);

X is selected from the group consisting of $CH_2$, O, S, SO and $SO_2$;

m and n are independently zero or the integer 1 or 2;

p is an integer from 1 to 5; and the agronomically acceptable acid addition salts thereof.

2. A compound according to claim 1 wherein $R^3$ is selected from the group consisting of hydrogen, ($C_1$-$C_{12}$) alkyl, ($C_6$-$C_{10}$) aryl or ($C_7$-$C_{11}$) aralkyl, or ($C_6$-$C_{10}$) aryl or ($C_7$-$C_{11}$) aralkyl substituted with up to three substituents selected from the group consisting of halogen, ($C_1$-$C_4$) alkyl, ($C_1$-$C_4$) alkoxy, and nitro.

3. A compound according to claim 1 having the formula

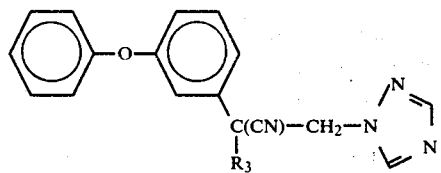

and the agronomically acceptable acid addition salts thereof.

4. A compound according to claim 1 having the formula

and the agronomically acceptable acid addition salt thereof.

5. A fungicidal composition which comprises an agriculturally acceptable carrier and as the active ingredient a fungicidally effective amount of a compound according to claim 1.

6. A method for controlling phytopathogenic fungi which comprises applying to the plant, the plant seed, or the plant habitat, a fungicidally effective amount of a compound according to claim 1.

* * * * *